(12) United States Patent
Flory et al.

(10) Patent No.: US 8,636,008 B2
(45) Date of Patent: Jan. 28, 2014

(54) ENDOTRACHEAL TUBE HOLDER

(75) Inventors: James M. Flory, Roselle, IL (US); Mark A. Kauth, Elgin, IL (US); Timothy F. Camodeca, Hampshire, IL (US)

(73) Assignee: ParaProducts, Inc, South Elgin, IL (US)

( * ) Notice: Subject to any disclaimer, the term of this patent is extended or adjusted under 35 U.S.C. 154(b) by 1259 days.

(21) Appl. No.: 10/538,425

(22) PCT Filed: Dec. 8, 2003

(86) PCT No.: PCT/US03/38845
§ 371 (c)(1),
(2), (4) Date: Feb. 5, 2008

(87) PCT Pub. No.: WO2004/052267
PCT Pub. Date: Jun. 24, 2004

(65) Prior Publication Data
US 2008/0202529 A1    Aug. 28, 2008

Related U.S. Application Data

(60) Provisional application No. 60/432,679, filed on Dec. 11, 2002.

(51) Int. Cl.
*A61M 11/00* (2006.01)

(52) U.S. Cl.
USPC .................................. 128/207.14; 128/207.15

(58) Field of Classification Search
USPC ............. 128/207.14, 207.15, 200.24, 200.26; 604/174, 177, 178; 30/102, 96, 97; 83/820; 7/157, 158, 160, 163; 29/896.1, 270, 278; 269/3, 6, 45, 249
See application file for complete search history.

(56) References Cited

U.S. PATENT DOCUMENTS

| | | | | |
|---|---|---|---|---|
| 2,534,690 | A | * 12/1950 | Young, Jr. et al. | ............ 248/68.1 |
| 3,602,227 | A | 8/1971 | Andrew | |
| 3,894,706 | A | * 7/1975 | Mizusawa | ..................... 248/68.1 |
| 3,940,823 | A | * 3/1976 | Rosenbeck | .............. 15/250.454 |
| 3,946,742 | A | 3/1976 | Eross | |
| 4,114,626 | A | 9/1978 | Beran | |
| 4,118,838 | A | * 10/1978 | Schiefer et al. | ............. 24/115 R |
| 4,202,087 | A | * 5/1980 | Wilderman | ................... 166/243 |
| 4,249,529 | A | 2/1981 | Nestor et al. | |
| 4,270,529 | A | 6/1981 | Muto | |
| 4,326,515 | A | 4/1982 | Shaffer et al. | |
| 4,331,144 | A | 5/1982 | Wapner | |
| 4,351,331 | A | 9/1982 | Gereg | |
| 4,360,025 | A | 11/1982 | Edwards | |
| 4,392,857 | A | 7/1983 | Beran | |
| 4,449,527 | A | 5/1984 | Hinton | |
| 4,516,293 | A | 5/1985 | Beran | |
| 4,683,882 | A | 8/1987 | Laird | |
| 4,699,616 | A | 10/1987 | Nowak et al. | |
| 4,744,358 | A | 5/1988 | McGinnis | |
| 4,774,944 | A | 10/1988 | Mischinski | |
| 4,823,919 | A | * 4/1989 | Hayatdavoudi | ................. 188/67 |

(Continued)

*Primary Examiner* — Steven Douglas
(74) *Attorney, Agent, or Firm* — Erickson Law Group, PC

(57) ABSTRACT

An endotracheal tube holder for restraining an endotracheal tube in a patient's mouth includes a base that is strapped to the patient's head. The base includes a tube-securing block and clip-securing blocks. A separate, U-shaped clip is engagable in ratchet fashion to the base between the tube-securing block and the clip restraining blocks to secure the endotracheal tube to the tube-securing block.

20 Claims, 14 Drawing Sheets

(56) References Cited

U.S. PATENT DOCUMENTS

| | | | |
|---|---|---|---|
| 4,832,019 A | 5/1989 | Weinstein et al. | |
| 4,874,380 A | 10/1989 | Hesketh | |
| 4,906,234 A | 3/1990 | Voychehovski | |
| 4,932,943 A | 6/1990 | Nowak | |
| 4,936,530 A * | 6/1990 | Wollar | 248/71 |
| 4,986,815 A | 1/1991 | Schneider | |
| 5,009,227 A | 4/1991 | Nieuwstad | |
| 5,069,206 A | 12/1991 | Crosbie | |
| 5,073,170 A | 12/1991 | Schneider | |
| 5,076,269 A | 12/1991 | Austin | |
| 5,105,807 A | 4/1992 | Kahn et al. | |
| 5,167,630 A | 12/1992 | Paul | |
| 5,224,935 A | 7/1993 | Hollands | |
| 5,237,988 A | 8/1993 | McNeese | |
| 5,320,097 A | 6/1994 | Clemens et al. | |
| 5,342,324 A * | 8/1994 | Tucker | 604/264 |
| 5,345,931 A | 9/1994 | Battaglia, Jr. | |
| 5,419,319 A | 5/1995 | Werner | |
| 5,437,273 A | 8/1995 | Bates et al. | |
| 5,490,504 A | 2/1996 | Vrona et al. | |
| 5,513,633 A | 5/1996 | Islava | |
| 5,551,421 A | 9/1996 | Noureldin et al. | |
| 5,653,232 A | 8/1997 | Rogers et al. | |
| D395,505 S | 6/1998 | Noonan et al. | |
| 5,775,778 A * | 7/1998 | Riley et al. | 297/440.1 |
| 5,806,516 A | 9/1998 | Beattie | |
| 5,829,430 A | 11/1998 | Islava | |
| 5,894,840 A | 4/1999 | King | |
| 5,996,581 A | 12/1999 | Duch | |
| 6,010,484 A | 1/2000 | McCormick et al. | |
| 6,029,668 A * | 2/2000 | Freed | 128/207.17 |
| 6,050,263 A | 4/2000 | Choksi et al. | |
| 6,067,985 A | 5/2000 | Islava | |
| 6,126,122 A * | 10/2000 | Ismert | 248/74.1 |
| D434,496 S | 11/2000 | Choksi et al. | |
| 6,409,220 B1 * | 6/2002 | Wing et al. | 285/12 |
| 6,526,978 B2 * | 3/2003 | Dominguez | 128/207.14 |

\* cited by examiner

ENDOTRACHEAL TUBE HOLDER

This application is a 35 USC 371 of PCT/US2003/038845 which claims the benefit of U.S. Provisional Application No. 60/432,679 filed Dec. 11, 2002.

TECHNICAL FIELD OF THE INVENTION

The present invention relates generally to an endotracheal tube-holding apparatus and more particularly to an endotracheal tube holder in which an endotracheal tube is secured to be correctly position within the patient's mouth and trachea.

BACKGROUND OF THE INVENTION

An endotracheal tube holder is used on a patient for securing and holding in place an endotracheal tube. The endotracheal tube is a narrow, hollow tube which is inserted through a patient's mouth and into the trachea. The purpose of the tube is to provide oxygen to the lungs of the patient to support respiration.

In use, a portion of the endotracheal tube is left to protrude from the patient's mouth so that a ventilation device can be attached to the end of the tube to provide forced or assisted ventilation to the patient. The endotracheal tube holder is placed on the patient's face, having an opening in registry with the patient's mouth. The tube is held in place by attaching the tube to the holder and then securing the holder to the patient.

The tube holder prevents the tube from moving longitudinally into or out of the patient's trachea. Unwanted movement could result in the loss of oxygen to the patient's lungs, and the loss of respiration, and possibly injury or death of the patient.

Endotracheal tubes are used under several conditions such as in the ventilation of a patient during anesthesia and resuscitation, as well as during critical care that commonly arises not only in the hospital but also while a patient is being treated at an accident or while being were transported.

Endotracheal tube holders are known which include a faceplate which engages the patient's lips and/or adjacent areas and which carries a tube-holding device for securing an endotracheal tube within a patient's mouth and trachea. For example, U.S. Pat. Nos. 5,829,430; 5,551,421; 5,513,633; 5,829,430; 5,320,097; 5,237,988; 4,832,019 and 4,516,293, discloses such devices.

The present inventor has recognized that it would be desirable to provide an endotracheal tube holder which is cost effectively manufactured and which is quickly and reliably usable by medical personnel, especially by paramedics at accident and injury locations.

SUMMARY OF THE INVENTION

The endotracheal tube holder of the invention comprises an endotracheal tube-retaining base and an endotracheal tube-retaining clamp. The base and clamp act together to secure an endotracheal tube to a patient. A strap is used to secure the holder to the patient's head.

The base is configured to rest on the patient's face, substantially over the patient's mouth. The base includes two arms which straddle the patient's mouth. The two arms each include a hook and loop surface (such as a VELCRO surface) on a top side thereof. The strap is wrapped around the patient's head, and pressed to, and thereby fastened to, the hook and loop surfaces.

According to a preferred embodiment, the base can include a soft surface, such as a foam pad, on a bottom side thereof for the patient's comfort. Molded on a top side of the retaining base are an endotracheal tube-securing block and two retaining clip-securing blocks.

A separate piece, endotracheal tube-retaining clip is used to hold the endotracheal tube to the retaining base. The endotracheal tube is positioned between the retaining clip and the endotracheal tube-securing block. The area where the retaining clip and the securing block interface with the endotracheal tube is shaped so that it will secure a hollow tube between the sizes of about 3 mm and 12 mm. The endotracheal tube-retaining clip is held in place by teeth on outside-facing surfaces thereof which engage corresponding teeth on inside-facing surfaces of the retaining clip-securing blocks. The interface holds the retaining clip in place until the user wishes to release the clip. To release the clip, the retaining clip is squeezed which separates the coacting teeth.

An alternate embodiment of the invention includes a curved section protruding from the bottom of the retaining base which functions as a bite block. The bite block prevents the patient from clamping his teeth down on the endotracheal tube and preventing oxygen from reaching the lungs.

The endotracheal tube holder is secured to the patient's head and face by means of a strap assembly. A strap assembly is attached to the retaining base at a strap loop on one end of the base. A strap is preferably a one-piece hook and loop (such as VELCRO) fabric material which can be separated into two strips along its length by means of a serration, or other type of line of weakness, extending longitudinally along a centerline of the strap. In use, the strap is wrapped around a patient's head and pulled apart into two strips, wherein the two strips are placed on the top side of the straddling arms of the retaining base to engage the hook and loop surfaces on the top surface of the arms.

Numerous other advantages and features of the present invention will be become readily apparent from the following detailed description of the invention and the embodiments thereof, from the claims and from the accompanying drawings.

DETAILED DESCRIPTION OF THE PREFERRED EMBODIMENTS

Figure 1:
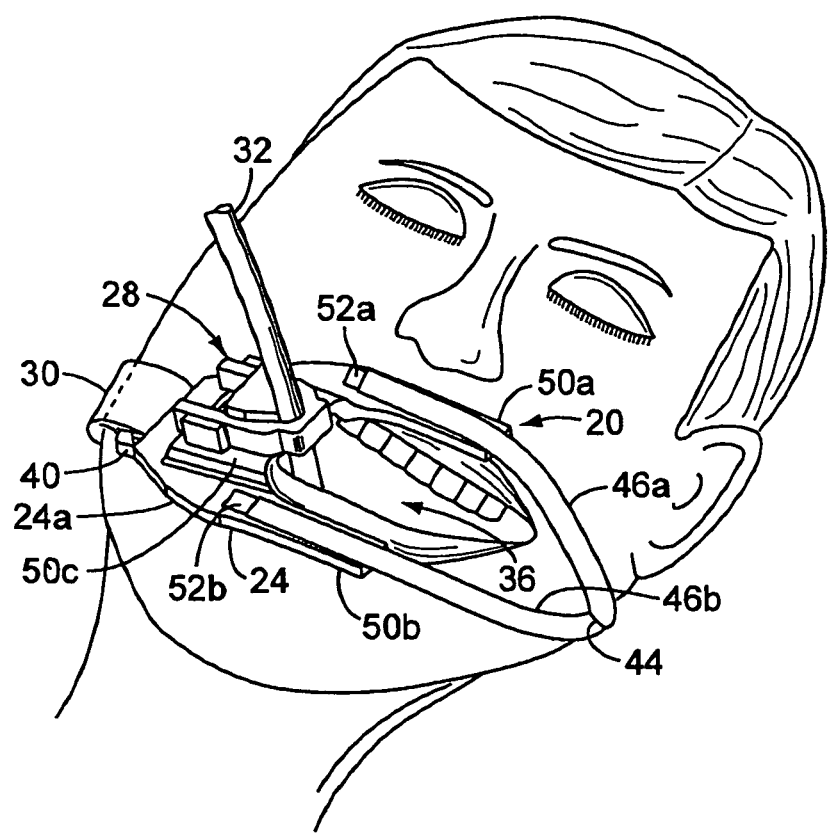
FIG. 1 is a perspective view of the endotracheal tube holder of the present invention strapped to a patient.

While this invention is susceptible of embodiment in many different forms, there are shown in the drawings, and will be described herein in detail, specific embodiments thereof with the understanding that the present disclosure is to be considered as an exemplification of the principles of the invention, and is not intended to limit the invention to the specific embodiments illustrated.

FIG. 1 illustrates the endotracheal tube holder 20 of the invention strapped to a patient. The holder 20 includes a base 24 and a tube-holding assembly 28. The base 24 is secured onto the patient by a strap 30. The tube-holding assembly 28 holds an endotracheal tube 32 which enters the patient's mouth 36 and is positioned in the trachea.

The strap 30 is threaded into a strap loop 40 formed on an end of the base 24 and secured upon itself to affix the strap 30 to the base 24. The strap is preferably a one-piece hook and loop (such as VELCRO) fabric material which can be separated into two strips 46a, 46b along its length by means of a serration, or other type of line of weakness, extending longitudinally along an approximate centerline 44 of the strap 30.

The base 24 is configured to rest on the patient's face, substantially over the patient's mouth 36. The base 24 includes straddling arms 50a, 50b extending from a raised central platform 50c. The two arms 50a, 50b straddle the patient's mouth. The two arms each include a hook and loop surface 52a, 52b on a top side thereof. The hook and loop surface can be applied to the top surface of the arms 50a, 50b for example by the use of hook and loop tape, such as a VELCRO tape. When the strap 30 is wrapped around the patient's head, the strips 46a, 46b can be fastened to the hook and loop surfaces. The base 24 can include a soft surface, such as a foam pad, on a bottom side 24a thereof for the patient's comfort.

Figure 2:
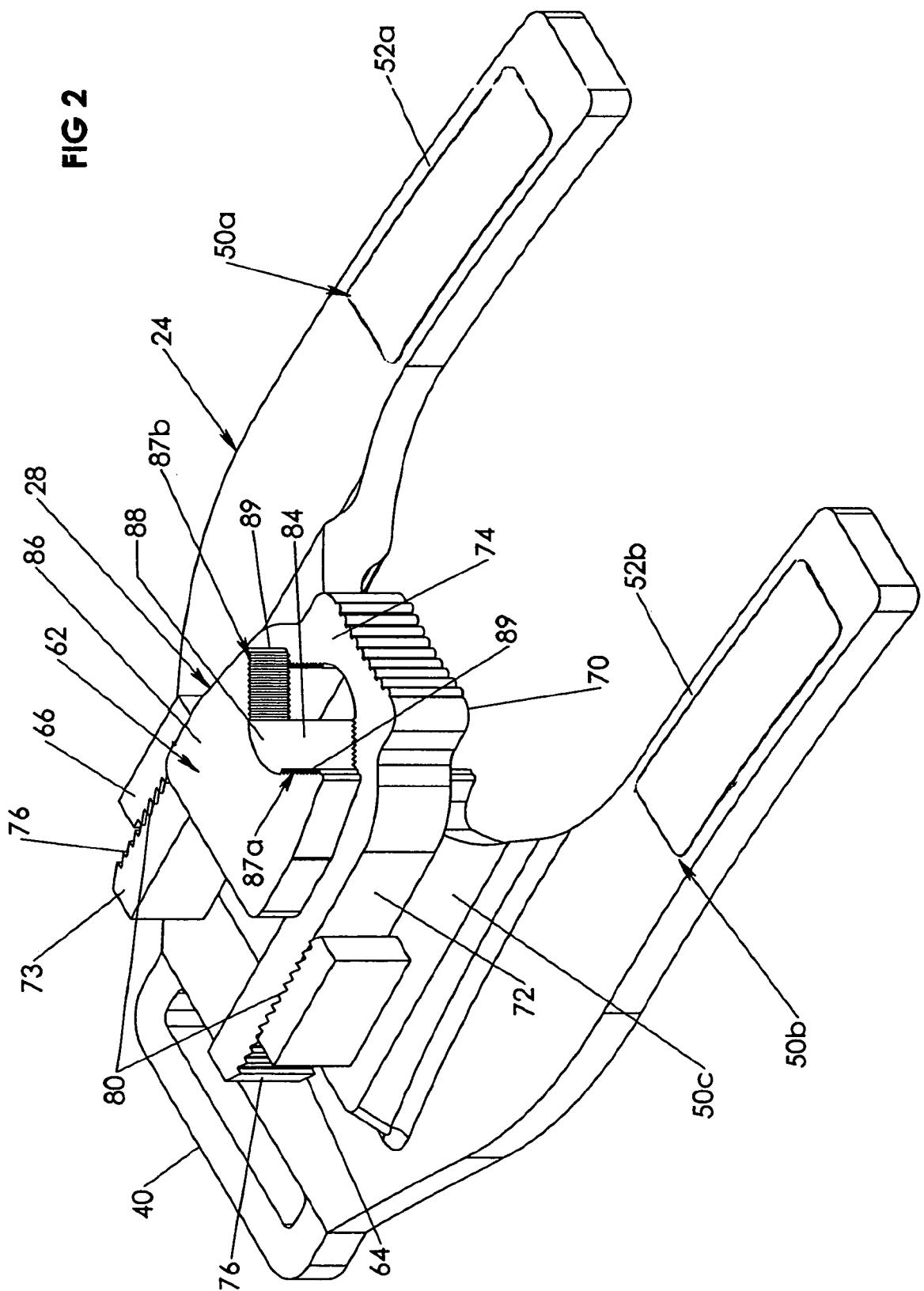
FIG. 2 is an enlarged perspective view of the tube holder of FIG. 1 including a base and a clip.

The base 24 and the tube-holding assembly 28 are shown in more detail in FIG. 2. Molded on a top side 24b of the retaining base 24 are an endotracheal tube-securing block 62 and two retaining clip-securing blocks 64, 66. A separate piece, endotracheal tube-retaining clip 70 is used to hold the endotracheal tube 32 to the retaining base 24. The retaining clip 70 is substantially U-shaped, with legs 72, 73 extending from a base end 74. The endotracheal tube 32 is positioned between the retaining clip 70 and the endotracheal tube-securing block 62. The surface area between the retaining clip 70 and the securing block 62 that contact the endotracheal tube 32 is shaped so that it will secure a hollow tube between the sizes of about 3 mm and 12 mm.

The endotracheal tube-retaining clip 70 is held in place by teeth 76 on outside-facing surfaces of the legs 72, 73 which engage corresponding teeth 80 on inside-facing surfaces of the retaining clip-securing blocks 64, 66. The coacting teeth 76, 80 hold the retaining clip 70 in place until the user wishes to release the clip 70. To release the clip 70, the legs 72, 73 are squeezed together which separates the coacting teeth 76, 80.

The securing block 62 includes a post 84 (shown more clearly in FIGS. 4 and 5) and a cap 86. The cap 86 includes a substantially concave tube-receiving area 88 which includes substantially planar areas 87a, 87b with tube-engaging teeth 89. The cap 86 has a greater lateral dimension than the post 84 such that the legs 72, 73 of the clip straddle the post 84, while allowing some clearance so that the legs 72, 73 can be squeezed together to release the clip from the blocks 64, 66.

The legs 72, 73 slide snugly, in a height direction, beneath the overhang of the cap 86 and the raised central platform 50c.

Figure 3:
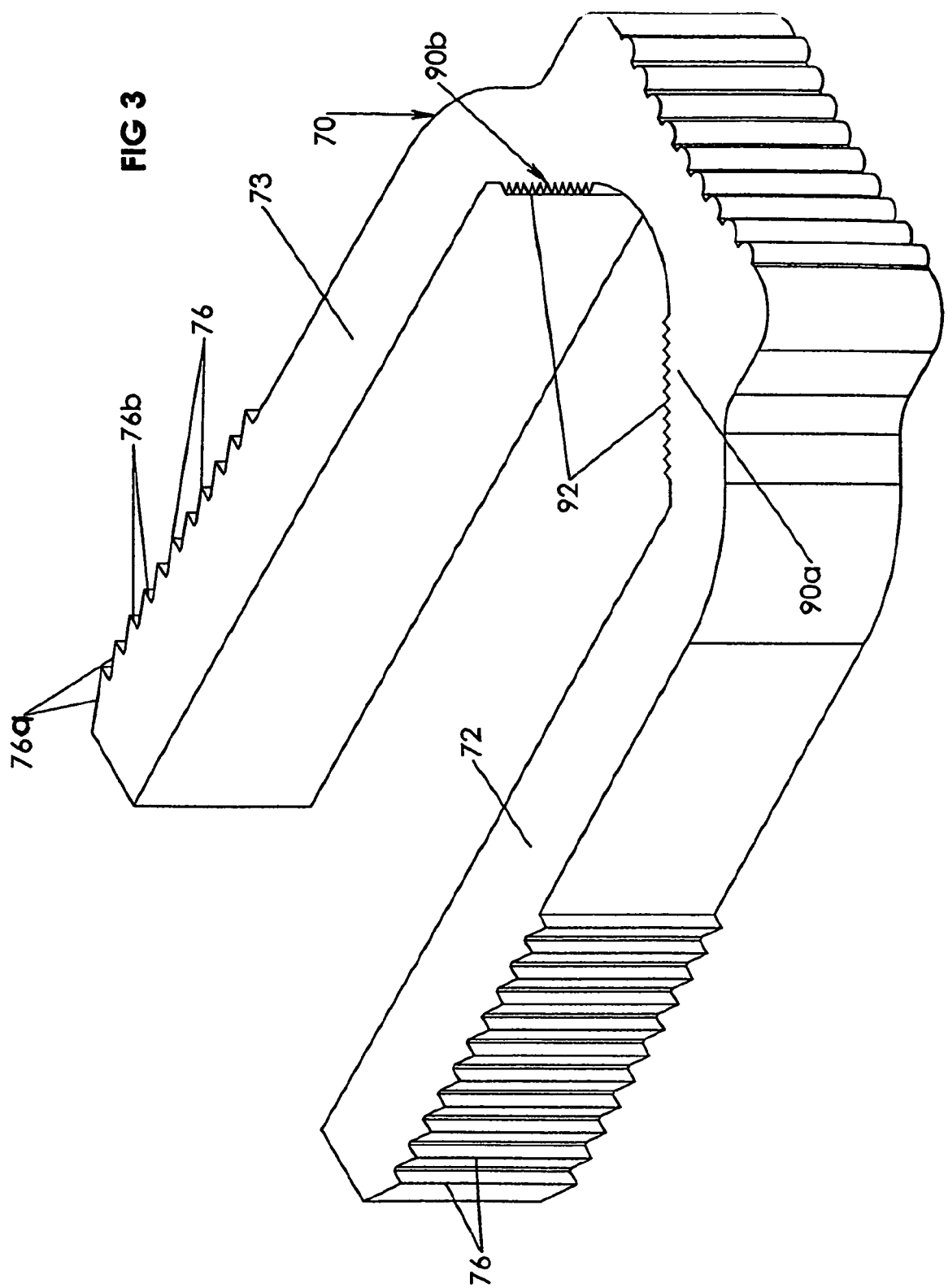
FIG. 3 is an enlarged perspective view of the clip of the tube holder of FIG. 2.

FIG. 3 illustrates the clip 70 in detail. The teeth 76 have gradually sloped sides 76a facing in a direction leading into engagement with the clip-retaining blocks 64, 66, and steep backsides 76b. The teeth 80 of the blocks 64, 66 also have gradually sloped sides facing the direction of insertion of the clip and steep front sides. The gradually sloped sides of the teeth 76, 80, which come into an engagement as the clip 70 is engage to the blocks 64, 66, allow for locking of the clip 70 to the blocks 64, 66 with minimal force. The backsides 76b of the teeth 76, in abutting engagement with the front sides of the teeth 80, prevent a force in a direction opposite to the insertion direction from removing the clip 70 from the blocks 64, 66, unless the legs 72, 73 are first squeezed together to disengage the teeth 76, 80. The clip 70 also includes substantially planar tube-gripping regions 90a, 90b having teeth 92.

Figure 4:
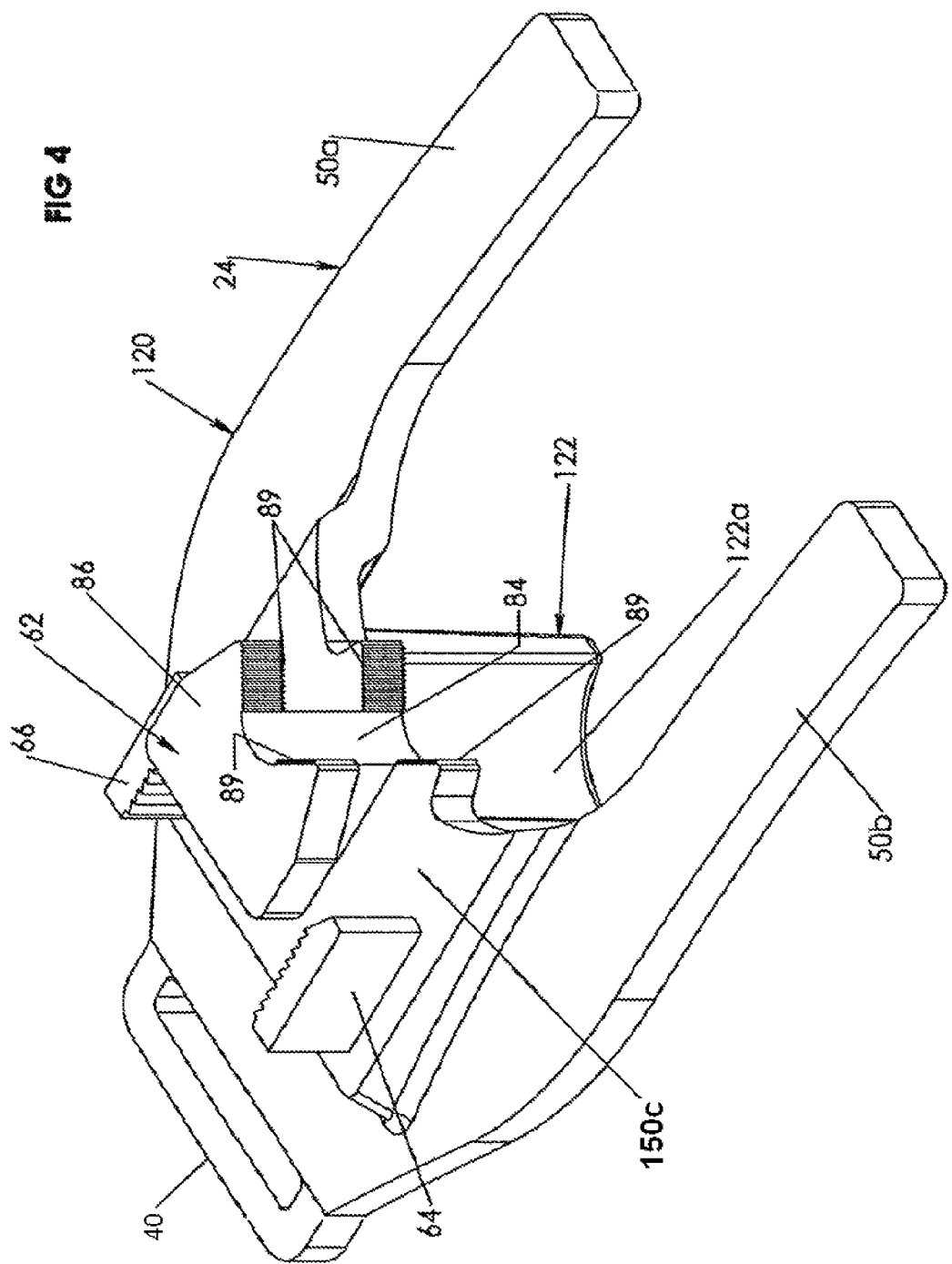
FIG. 4 is an enlarged perspective view of an alternate tube holder base of the invention.
Figure 5:
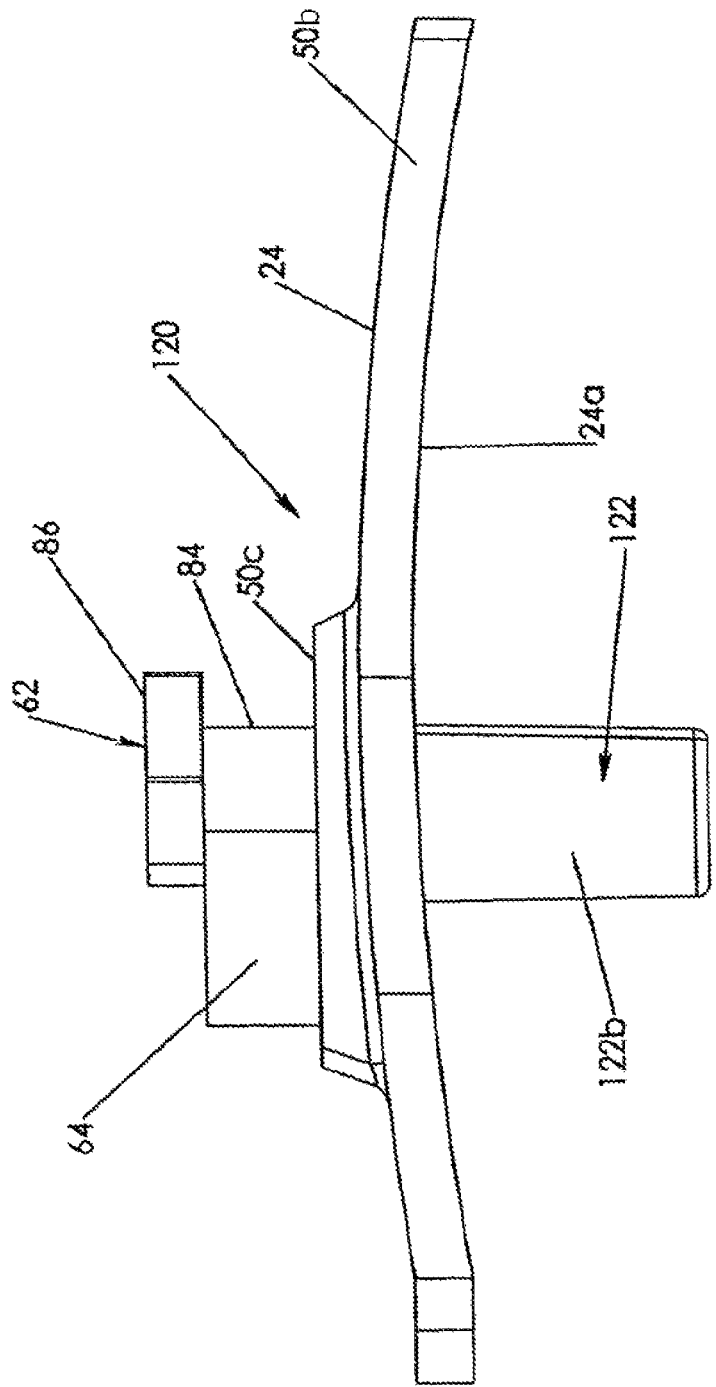
FIG. 5 is a side view of the tube holder base of FIG. 4.

FIGS. 4 and 5 illustrate an alternate embodiment holder 120 that includes a curved section 122 protruding from the bottom of the retaining base 24 which functions as a bite block. The curved section 122 includes a concave, semi-cylindrical inside surface 122a and a convex, semi-cylindrical outside surface 122b. The curved section 122 prevents the patient from clamping his teeth down on the endotracheal tube 32 and preventing oxygen from reaching the lungs. The curved section 122 can also be used on an alternate base 124 described below in FIGS. 6-8.

FIG. 5 also illustrates that the bottom 24a of the base 24 has a generally curved profile allowing the base 24 to fit comfortably on a patient's face.

Figure 6:
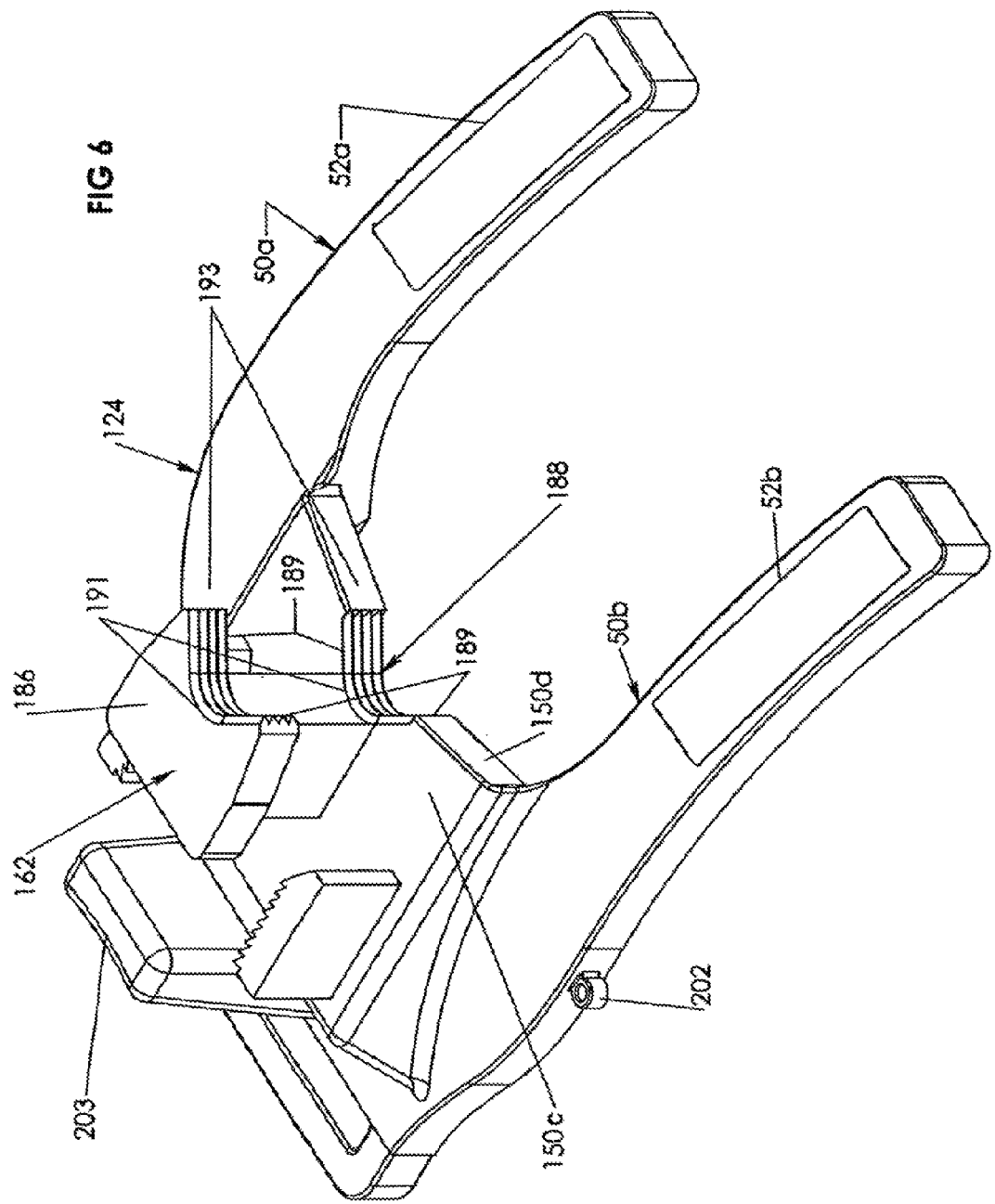
FIG. 6 is a perspective view of a further alternate embodiment base for the tube holder.
Figure 7:
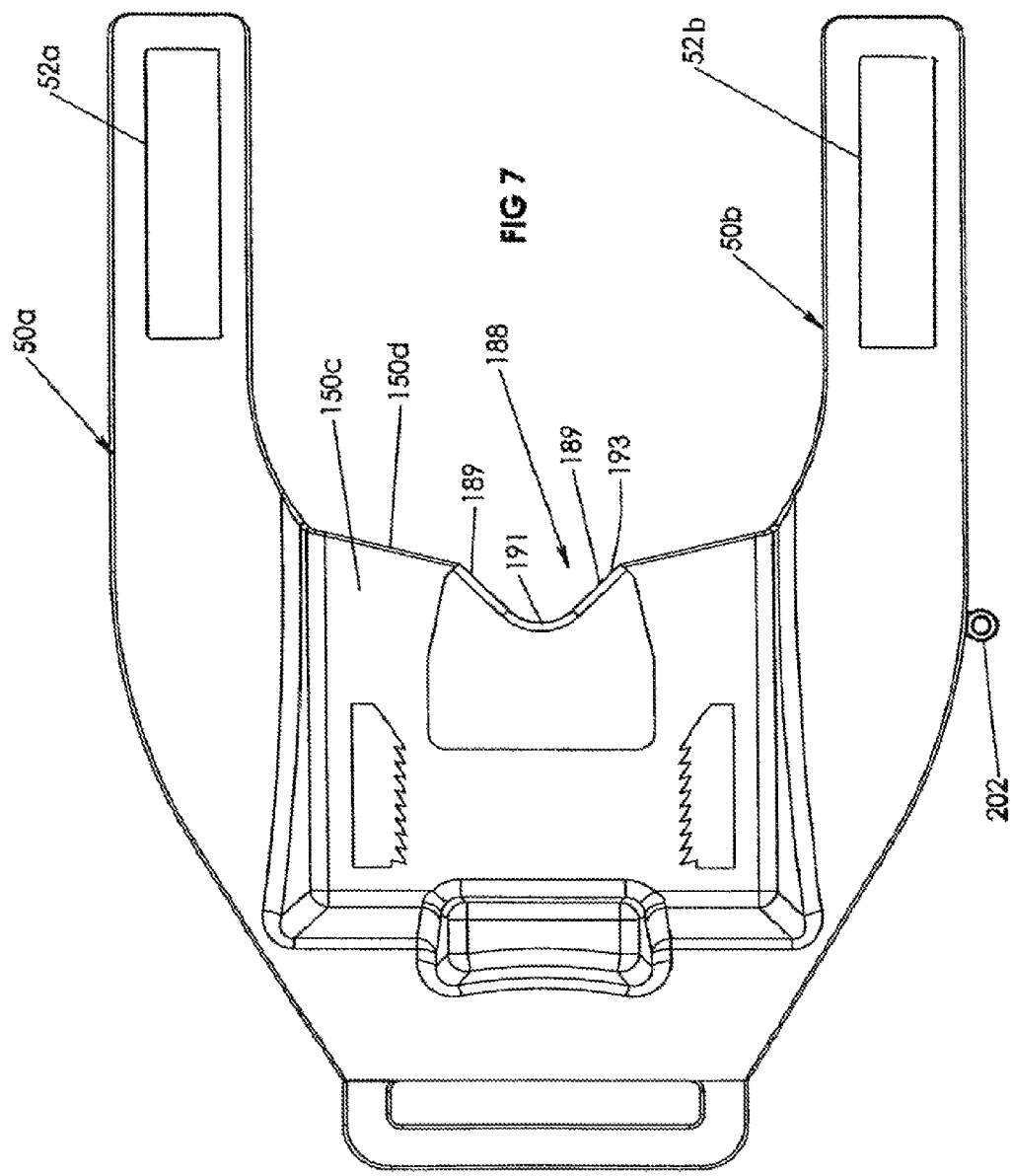
FIG. 7 is a plan view of FIG. 6.
Figure 8:
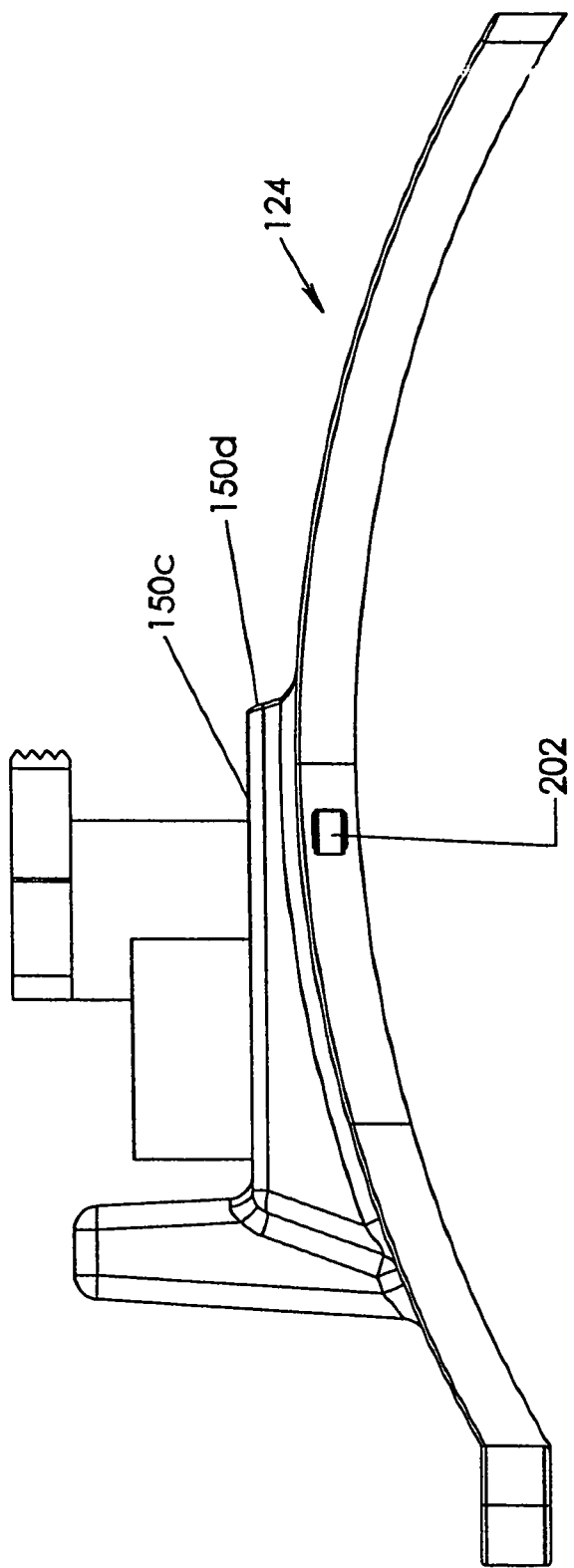
FIG. 8 is a side view of the base of FIG. 6.

FIGS. 6-8 illustrate an alternate base 124 having an alternate tube-securing block 162. The base 124 can be engaged by the clip 170 described below. The base 124 is similar to the previously described base 24 except as noted. The concave tube receiving area 188 is recessed from a front edge 150d of a raised central platform 150c of the base 124. The concave area is formed by planar areas 189 carried on the cap 186 and the raised central platform 150c; and curved central areas 191 carried on the cap 186 and the raised central area 150c. Horizontally extending teeth 193 are continuous through the respective areas 189, 191. The teeth 193 grip the tube held within the area 188. A tether loop 202 can be provided to connect the clip 70 or 170 onto the base 124 using a tether cord.

The base 124 further includes a brace block 203 that is used by the user to grip the block and clip and drive the clip onto the base 124 in latched condition via the teeth 76, 80.

Figure 9:
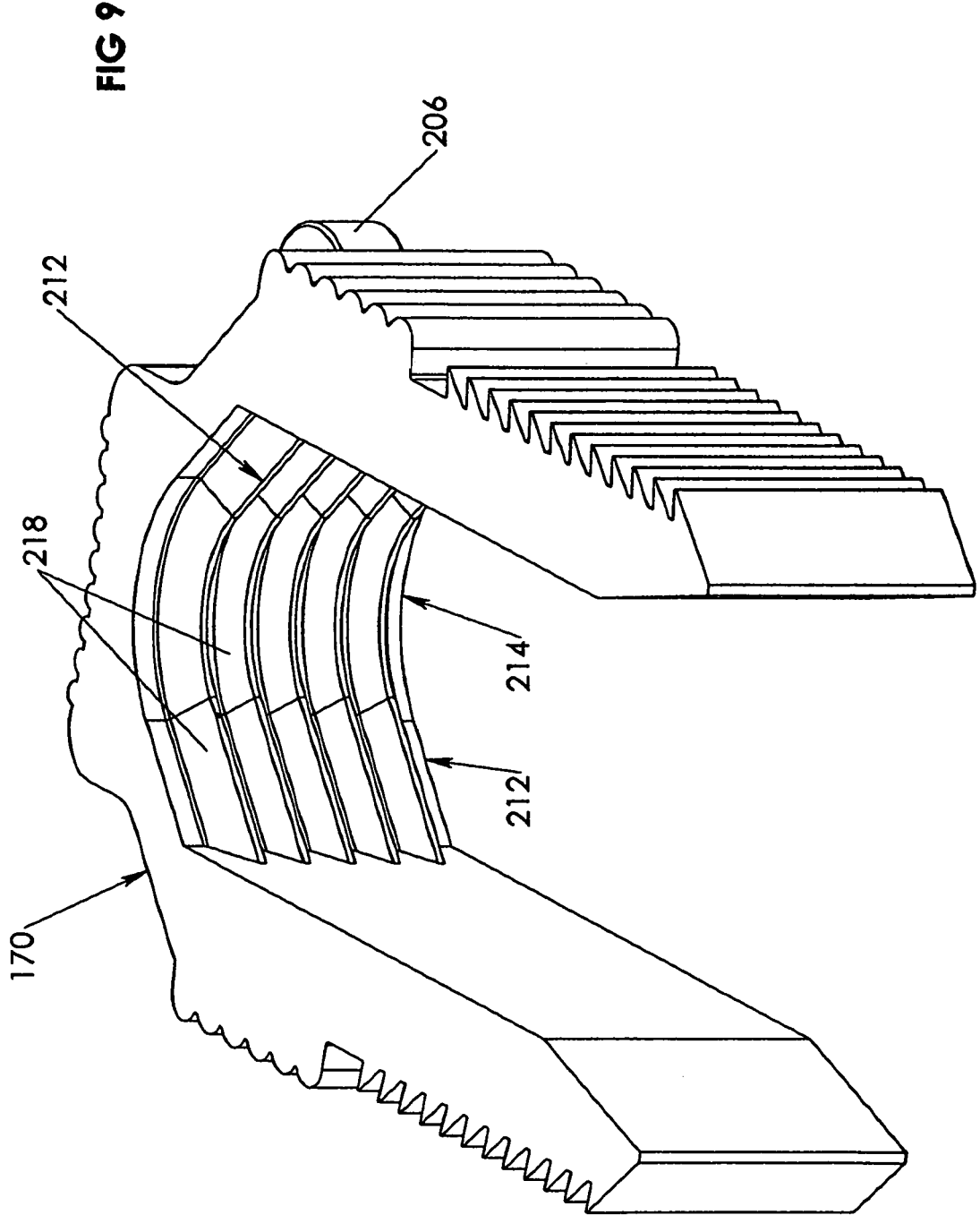
FIG. 9 is an enlarged perspective view of an alternate embodiment clip for a tube holder.
Figure 10:
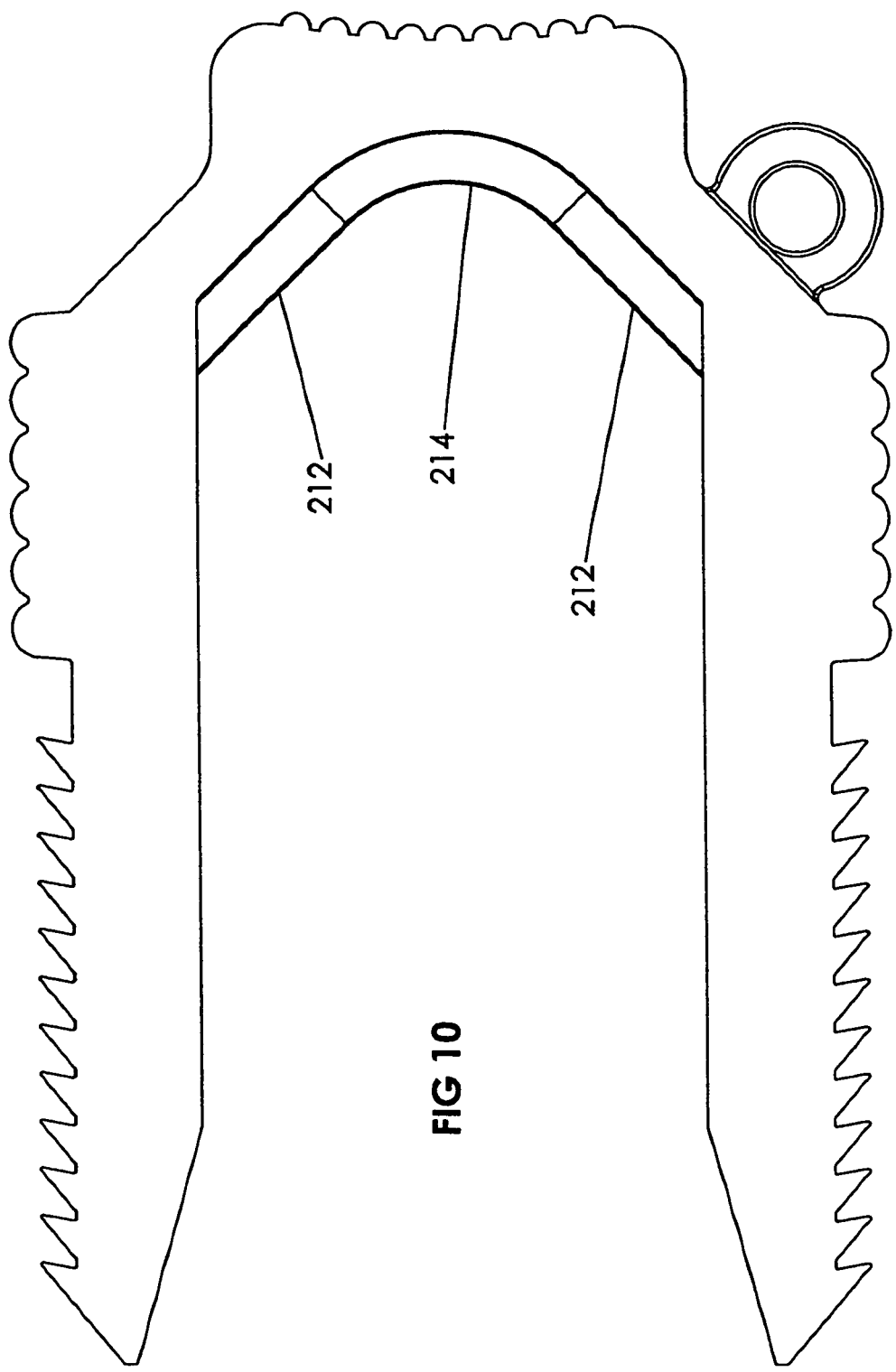
FIG. 10 is an enlarged plan view of the clip shown in FIG. 9.

FIGS. 9-10 illustrate an alternate clip 170. The alternate clip 170 is similar to the clip 70 except as noted. The clip could be used with any of the bases 24, 124 disclosed herein, but preferably is used with the base 124 of FIGS. 6-8. The clip 170 includes a loop 206 for retaining a tether cord that is to also be engaged to the loop 202 of the base 124. The clip 170 includes planar regions 212 connected by a curved region 214, all arranged to grip a tube when gripped by the holder. The regions 212, 214 include continuous horizontally disposed teeth 218 for gripping the tube.

Figure 11:
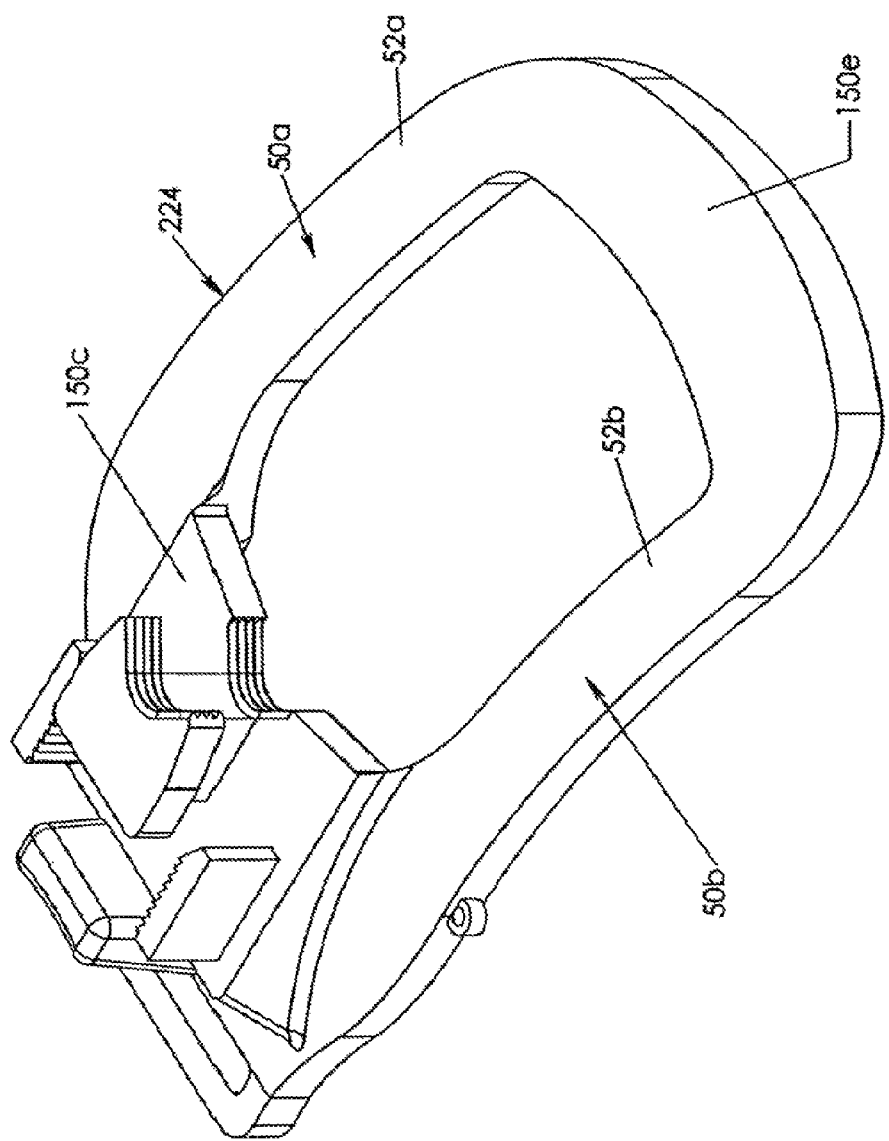
FIG. 11 is a perspective view of a further alternate embodiment base.
Figure 12:
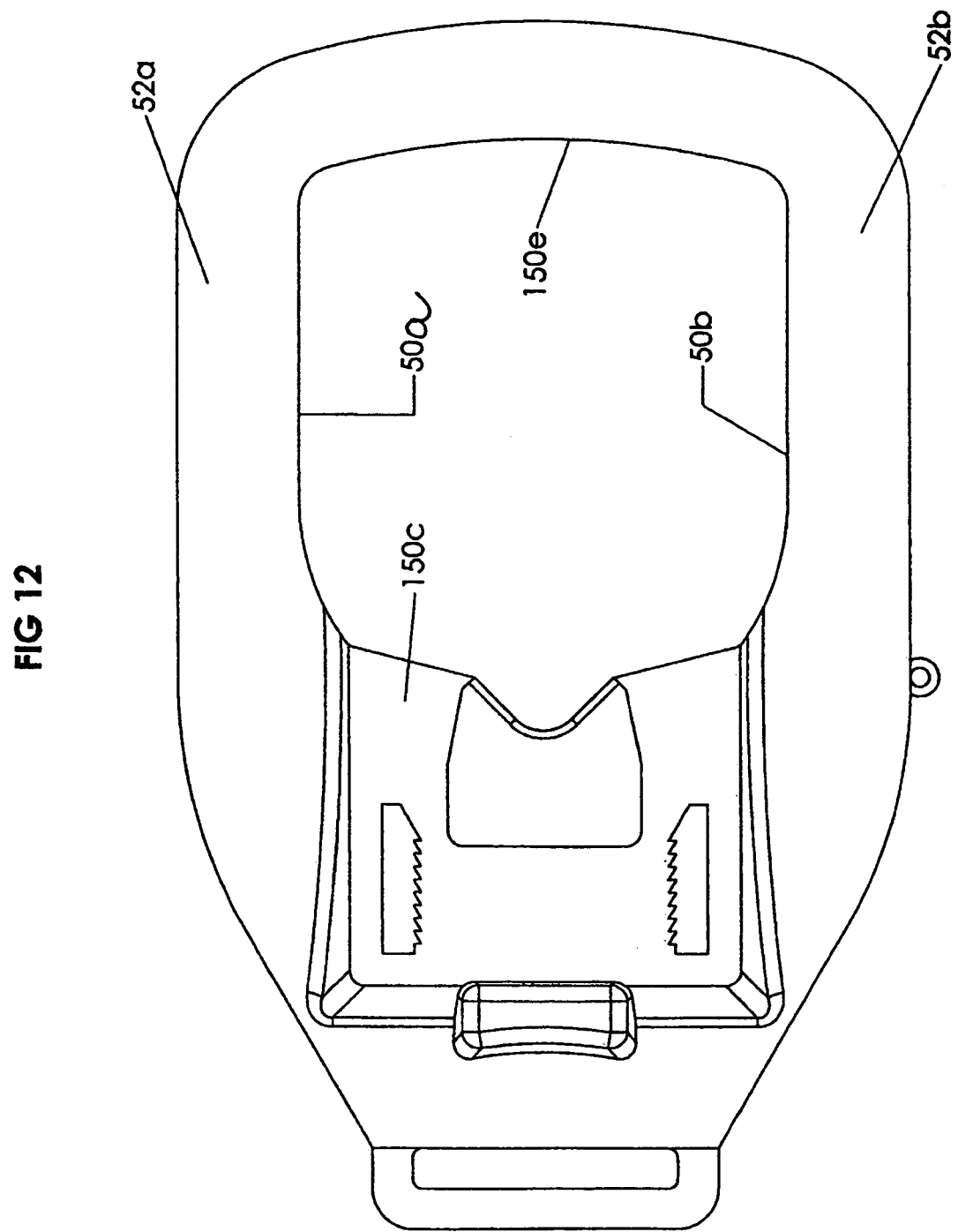
FIG. 12 is a plan view of the base of FIG. 11.

FIGS. 11 and 12 illustrate a further alternate base 224 that is effectively identical to the base 124 except the base includes an end plate 150e that connects the legs 50a, 50b.

Preferably, the bases 24, 124 and the retaining clips 70, 170, as well as the curved section 122 of the alternate embodiment of FIG. 4 are composed of plastic.

Figure 13:
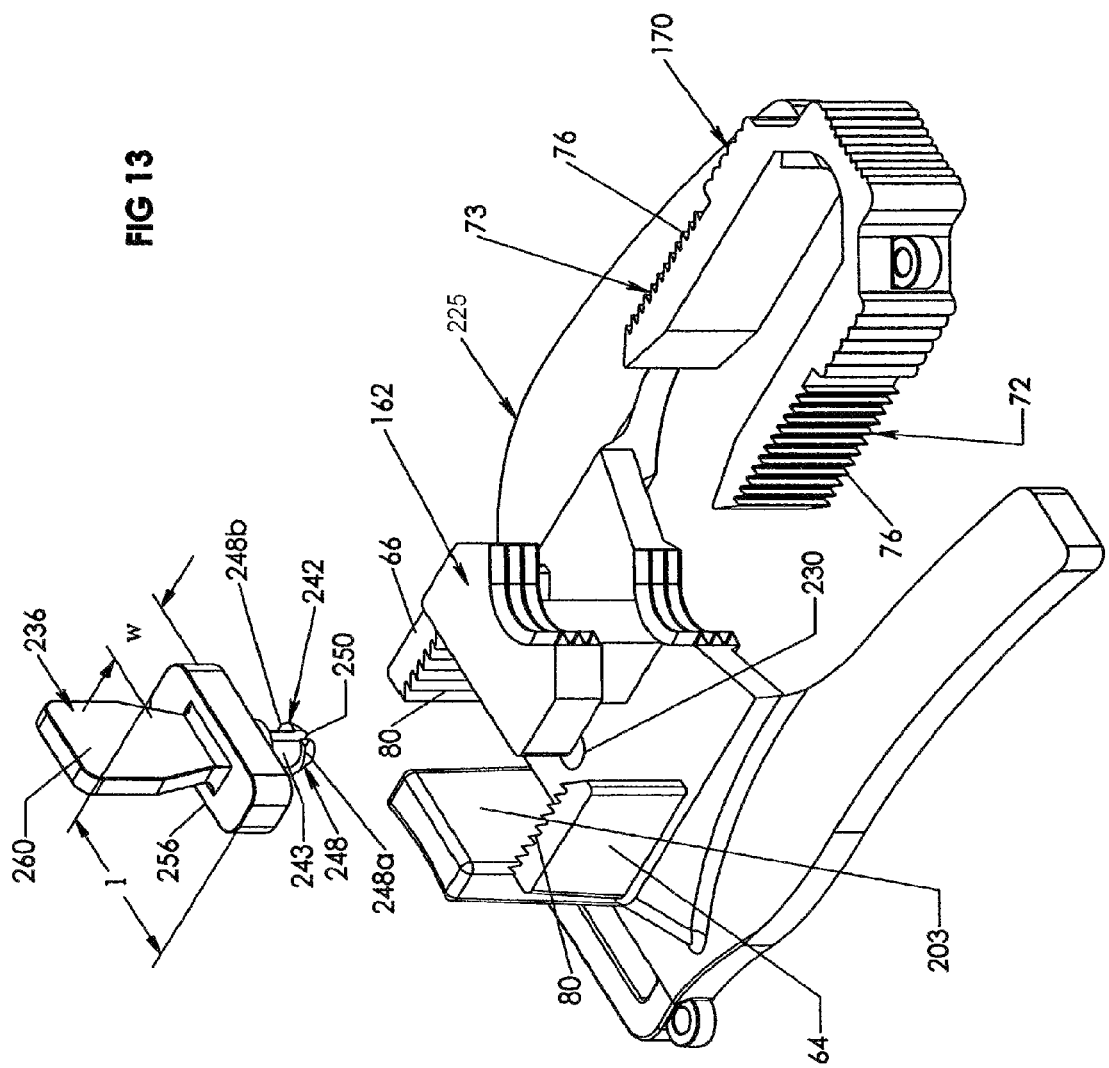
FIG. 13 is an exploded perspective view of another alternate embodiment tube holder.

FIG. 13 illustrates an alternate base 225, used with the clip 170. The base 225 is substantially identical to the base 124 of FIG. 6 but includes an aperture 230 behind the tube-securing block 162. A latch 236 is assembled to the base 225 by use of a snap fit pin 242 having a shaft 243 and a head 248, both split by a longitudinal slot 250. When the head 248 is pressed into the aperture 230 the shaft 243 and the head 248 are constricted by a decrease in the slot width such that the head 248 can pass through the aperture 230. The head 248 springs back under the base 225 to retain the latch 236 rotatably onto the base 225. The shaft 243 has an unconstricted diameter less than the diameter of the aperture 230 to be rotatable therein. The head 248 has an angled leading surface 248a to cause the constriction of the head and shaft and a shoulder surface 248b perpendicular to the shaft 243 which retains the pin, preventing retraction of the head 248 out of the aperture.

Figure 14:
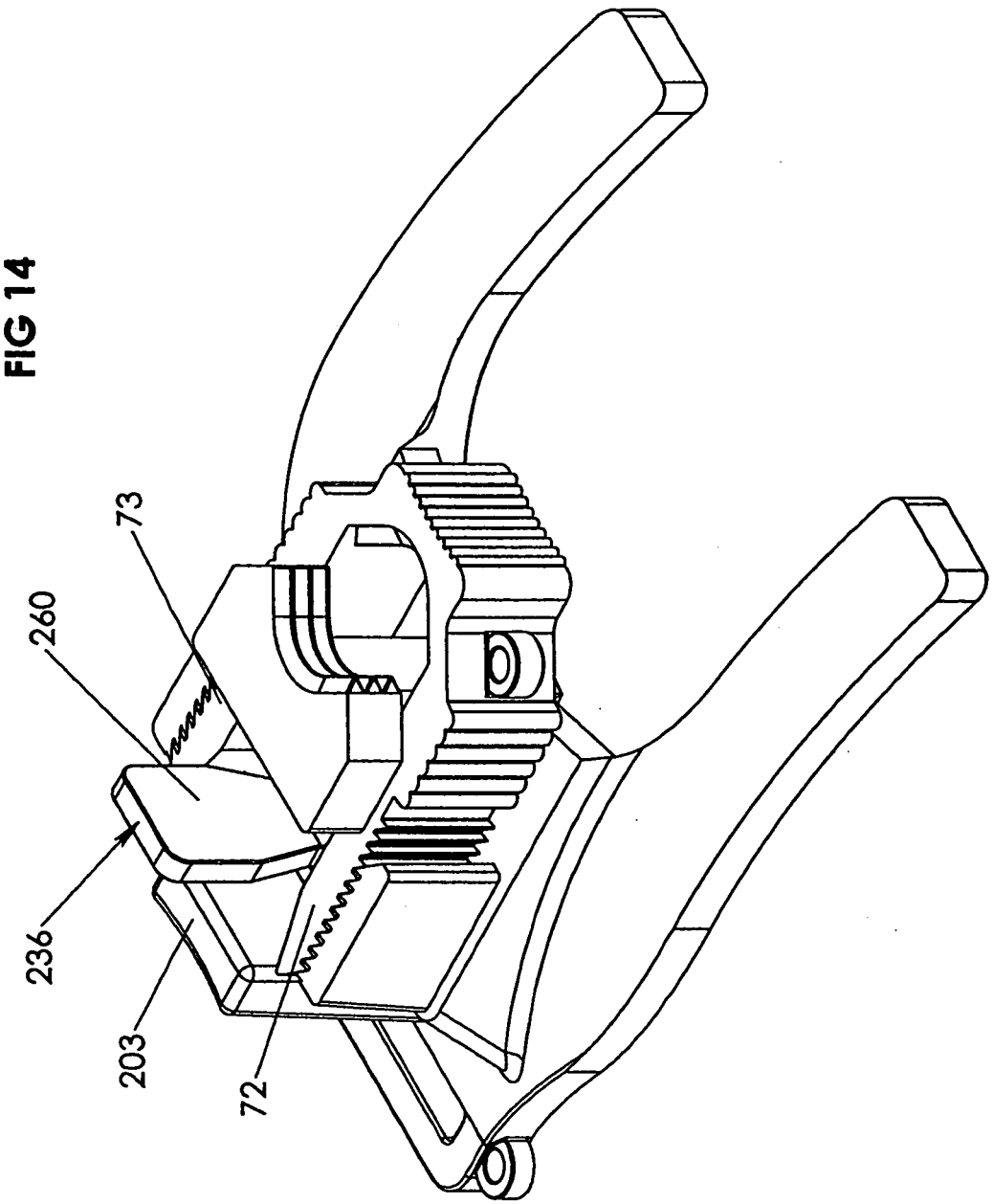
FIG. 14 is a perspective view of the alternate embodiment of FIG. 13 shown is an assembled condition.

The latch 236 includes a latch block 256 having a length l greater than a width w where the latch is installed onto the base 225 and turned to the orientation shown in FIGS. 13 and 14, the legs 72, 73 cannot be squeezed together to disengage the teeth 76, 80 of the leas 72, 73 and the clip-securing blocks 64, 66.

For removal and installation of the clip 170, the latch 236 is turned 90° from the position shown in FIGS. 13 and 14 by turning a latch handle 260. The smaller dimension w allows sufficient squeezing of the legs 72, 73 to remove or install the clip 170. The brace block 203 is located rearwardly of the legs so as not to interfere with squeezing the legs together to release the clip.

From the foregoing, it will be observed that numerous variations and modifications may be effected without departing from the spirit and scope of the invention. It is to be understood that no limitation with respect to the specific apparatus illustrated herein is intended or should be inferred.

The invention claimed is:

1. An endotracheal tube holder comprising:
a base having a bottom surface for bearing against a patient's face, and an opposite surface;
a tube-holding assembly having a tube-securing block fixed to said base and extending perpendicular to the opposite surface of said base and two clip-securing blocks arranged on opposite sides of said tube-securing block and also fixed to said base and extending perpendicular to the opposite surface of said base;
a tube-retaining clip having two legs and a base end portion, said two legs extending from said base end portion, said legs arranged to be engaged to said clip-securing blocks, with said legs straddling the tube-securing block, each leg inserted between a respective space between said tube-securing block and each respective clip-securing block wherein an endotracheal tube can be captured between said tube-securing block and said base end portion of said clip;
said tube-securing block arranged to hold the endotracheal tube in a direction generally perpendicular to the opposite surface of the base.

2. The tube holder according to claim 1, wherein one of said tube-securing block and said base end portion comprises tube-engaging teeth to grip said tube.

3. The tube holder according to claim 1, wherein each of said tube-securing block and said base end portion comprises a pair of planar areas of tube-engaging teeth.

4. The tube holder according to claim 1, wherein said clip-securing blocks each comprise first teeth on sides of said clip-securing blocks that face toward each other, and said legs comprise second teeth on sides of said legs facing away from each other wherein said first and second teeth are mutually engaged wherein said clip is installed to said base.

5. The tube holder according to claim 4, wherein said first and second teeth are angled in ratchet fashion to allow said clip to be installed by pushing said legs into said spaces while resisting retraction of said legs from engagement to said clip-securing blocks wherein said clip is pulled in an opposite direction.

6. The tube holder according to claim 5, wherein said legs can be squeezed together to release said first teeth from said second teeth to remove said clip from said tube-holding assembly.

7. The tube holder according to claim 1, wherein said base includes arms that straddle the patient's mouth extending in a transverse direction to the patient's face and said tube-securing block is arranged adjacent to a side of the patient's mouth.

8. The tube holder according to claim 1, comprising a restraining strap, wherein said base includes an attachment for said strap, wherein said strap can encircle the patient's head to hold the base to the patient's face.

9. The tube holder according to claim 1, wherein said base comprises a bite block that extends below said bottom surface into the patient's mouth to prevent closing together of the patient's upper and lower teeth.

10. The tube holder according to claim 1, wherein said retaining clip is separable from said base when said legs are disengaged from said clip-securing block.

11. The tube holder according to claim 10, further comprising a tether connected between said base and said clip.

12. The tube holder according to claim 1, wherein said base includes arms that straddle the patient's mouth extending in a transverse direction to the patient's face, and comprising a restraining strap, wherein said base includes an attachment for said strap, wherein said strap can encircle the patient's head to hold the base to the patient's face, wherein said strap comprises two parallel strap portions, and comprising hook and loop engagable fasteners applied between the top surface of the arms and the two parallel strap portions, and said strap comprises a base portion fixed to said base.

13. The tube holder according to claim 1, wherein said tube-securing block comprises an overhang position above each space, said overhang portions retain said clip to said base to prevent separation in a direction perpendicular to a top surface of said base.

14. An endotracheal tube holder comprising:
a base having a face-bearing surface;
a tube holding formation fixed to the base and having two first clip retaining portions, a clip hold down portion providing a cap that overhangs the base and forms a vertical clearance between the base and the cap, and a first tube-bearing surface;
a clip, separate from said base and having two second clip retaining portions, and a second tube-bearing surface, said clip at least partially slidable between said cap and said base, said second clip-retaining portions engagable with said first clip-retaining portions when said clip is slid at least partially between said cap and said base in a linear direction to latch said first and second tube-bearing surfaces tightly against an endotrachael tube located therebetween;
said clip sized and configured to have a thickness to be captured between the cap and the base to prevent removal of the clip from the base.

15. The tube holder according to claim 14, wherein said two first clip retaining portions comprises two clip-retaining blocks arranged on opposite sides of, and spaced from, said first tube-bearing surface; and said two second clip retaining portions comprises two legs, each leg engagable to a respective one clip-retaining block.

16. The tube holder according to claim 14, wherein said first and second tube-bearing surfaces each comprising planar areas of tube-engagable teeth.

17. The tube holder according to claim 14, wherein said base comprises spaced apart arms for bearing on the patient's face, straddling the patient's mouth, and a base portion connecting the arms and carrying said first tube-bearing surface, said first tube-bearing surface arranged to be located at a corner of the patient's mouth.

18. The tube holder according to claim 14, comprising a tether connecting said clip and said base.

19. The tube holder according to claim 14, further comprising a latch element, said latch element manually movable to prevent said two first clip retaining portions and said two second clip retaining portions from becoming disengaged from each other.

20. The tube holder according to claim 19, wherein said two first clip retaining portions comprises two clip-retaining blocks arranged on opposite sides of, and spaced from, said first tube-bearing surface, and said two second clip retaining portions comprises two legs, each leg engagable to a respective one clip-retaining block and said latch element is arranged to brace between said first and second legs to prevent disengagement of said legs and said clip-retaining blocks.

\* \* \* \* \*